United States Patent [19]

Mikalsen, deceased et al.

[11] Patent Number: 5,210,186

[45] Date of Patent: May 11, 1993

[54] METHOD FOR RECOVERY AND SEPARATION OF CHITIN, PROTEINS AND ASTAXANTHIN AND ESTERS THEREOF

[76] Inventors: Gunnar Mikalsen, deceased, late of Volda; by Ester Mikalsen, heiress, N-6100, Volda, Norway

[21] Appl. No.: 689,767

[22] PCT Filed: Nov. 15, 1989

[86] PCT No.: PCT/NO89/00119

§ 371 Date: Jul. 15, 1991

§ 102(e) Date: Jul. 15, 1991

[87] PCT Pub. No.: WO90/05765

PCT Pub. Date: May 31, 1990

[30] Foreign Application Priority Data

Nov. 18, 1988 [NO] Norway ................... 885150

[51] Int. Cl.$^5$ .................. C09B 61/00; A23J 1/04
[52] U.S. Cl. .................. 530/418; 530/419; 530/420; 426/540; 8/438; 8/646; 536/20; 536/124; 536/127; 536/128
[58] Field of Search ............ 530/418, 419, 420, 422, 530/423; 426/540; 536/20, 124, 127, 128; 8/438, 646

[56] References Cited

U.S. PATENT DOCUMENTS

| | | | |
|---|---|---|---|
| 3,862,122 | 1/1975 | Peniston | 536/20 |
| 4,119,619 | 10/1978 | Rogozhin | 530/418 |
| 4,199,496 | 4/1980 | Peniston et al. | 530/419 |
| 4,293,098 | 10/1981 | Muralidhara | 536/20 |
| 4,505,936 | 3/1985 | Meyers et al. | 426/540 |

FOREIGN PATENT DOCUMENTS 147365 3/1983 Norway .
PCT/DK86/-
    00034 10/1986 PCT Int'l Appl. .
1224172 3/1971 United Kingdom .

OTHER PUBLICATIONS

*The Chemistry of Natural Coloring Matters*, Fritz Mayer, (Abstract), American Chemical Society Monograph Series, 1943, pp. 66–67.
*Chemical Abstracts*, R. Blumberg, et al., "South African Fish products XXXII. Rock Lobster-Chitin Production From Processing Wastes", vol. 46, 1952, p. 11488.
*Chemical Abstracts*, K. Stern, et al., "Ovverdin, The Carotenoid-Protein Pigment Of The Egg Of The Lobster", vol. 32, 1938, p. 1791.
*Chemical Abstracts*, M. Ikeda, et al., "Purification of Chitin From Carapec of Penaeus Japonicus By A Proteolytic Bacterium", vol. 90, 1979, p. 278.
"On Ovoverdin, The Carotenoid-Protein Pigment Of The Egg Of The Lobster", K. Stern et al., from the Marine Biological Laboratory, Woods Hole, and the Laboratory of Physiological Chemistry and the Laboratory of Pharmacology and Toxicology, Yale University School of Medicine, New Haven, Oct. 6, 1937, pp. 473–475.

*Primary Examiner*—Ronald W. Griffin
*Attorney, Agent, or Firm*—Barnes & Thornburg

[57] ABSTRACT

A method is provided for recovering astaxanthin, astaxanthin carotenoids, astaxanthin esters, chitin and proteins from crustacean tissues containing such. The method comprises an initial extraction of crustacean tissue with boiling lye to form an alkaline extract and an extracted residue. The alkaline extract, upon cooling, forms separate layers from which can be recovered component protein, astaxanthin, astaxanthin carotenoids and astaxanthin esters. The lye extracted residue of chitin-containing such crustacean tissue is readily processed to provide chitin.

15 Claims, No Drawings

METHOD FOR RECOVERY AND SEPARATION OF CHITIN, PROTEINS AND ASTAXANTHIN AND ESTERS THEREOF

The present invention consists of a procedure for the production of astaxanthin and related carotenoids, astaxanthin esters, chitin, proteins and meat. Those products are recovered from plants, algae, bacteria, krill, shrimps and other crayfish and crustacea. The method comprises boiling the raw materials in a lye solution to form an alkaline extract and a residue which can be separated by filtration. Typically the alkaline extraction procedure is repeated and the extracts are combined. Upon cooling, the extracts separate into three phases, respectively having a lowest specific weight, an intermediate specific weight and a highest specific weight. The phase having the lowest specific weight upon neutralization yields two phases, the oily phase of which comprises astaxanthin esters. The phase with the highest specific weight upon neutralization yields solids consisting of astaxanthin and related carotenoids separable from the neutralized high specific weight phase by filtration. The alkaline extract phase having an intermediate specific weight contains protein components from the raw materials. That phase can be neutralized, treated to remove fluoride and heavy metal contaminants and thereafter acidified to precipitate extracted proteins. The residue obtained from the original lye solution extraction procedure is dried in concentration formic acid and thereafter dissolved in anhydride formic acid or another strong acid. The resulting acidic solution is filtered and diluted with water to precipitate chitin.

Astaxanthin and related carotenoids are used in the fish farming industry today as dies for colouring the fish meat of species which have red or pale red meat in natural habitats. During cultivation there is no feed that contains enough dye to give this colour flesh to such fish. These dyes are produced today by fermenting algae and synthesizing from a fermentation mixture. This approach is both expensive and time-consuming and necessitates the processing of large volumes of fermentation mixture.

So far there has been no product to meet the need for an inexpensive industrial process for producing astaxanthin and related carotenoids for the fish farming industry and other applications for the colouring of foodstuffs. The present invention describes a procedure which enables astaxanthin and related carotenoids to be produced on an industrial basis much cheaper than with present day technology. At the same time, the present invention is based on the exploitation of natural resources that are unexploitable or which represent a waste disposal problem. These include Antarctic krill; plants, bacteria and algae; and waste from the commercial processing of the meat in species such as shrimps, crayfish and crustacea. The present invention also helps to utilize the above-mentioned natural resources better, by using more of the raw material, either by improving the degree of utilization through the production of the required products, or by utilizing the same raw material to produce other types of products. Thus the present invention can for example be used to produce astaxanthin and related carotenoids astaxanthin esters, chitin, proteins and meat from Antarctic krill in a way that gives an extremely high degree of utilization of this raw material.

The shells of Antarctic krill are in addition the greatest unused source of protein in the world. However they cannot be used for feed or food because they contain too many toxic components such as fluorine and toxic heavy metals. With the means of production in the present invention, both the fluorine and the toxic heavy metals can be removed from the shells so that extensive use can be made of the proteins and chitin that can be produced from them.

These and other features of the invention become evident from the characterizing part of the Claims of Patent below.

The method in accordance with this invention will now be illustrated in greater detail by the following examples.

EXAMPLE 1

Krill

When the Antarctic krill is caught, the meat is squeezed out behind the cephalothorax using modified shrimp processing equipment. This extraction of the meat must be done within 3 to 4 hours of the time of catching to avoid contamination from the shell, head and cephalothorax which could affect the meat. As the autolysis of krill occurs very quickly and easily, this is another reason why the meat must be extracted within 4 hours of the time of the catch. After the meat has been squeezed out it has to be kept at below 40° C. until it is processed. The contaminants in krill are mainly the fluorine in the shell and toxic heavy metals such as cadmium, mercury, lead and zinc. There are high concentrations of cadmium in the cephalothorax and the content of the head.

The further treatment of the rest of the krill after the meat has been extracted, i.e., the shell, cephalothorax and the head with its content, here termed krill shell, can take alternative forms.

Alternative A

The krill shell is boiled in 1.0N NaOH for 30 min. then the extract is separated from the residue. The residue is then again boiled in 1.0N NaOH for 30 min. and extract is once more separated from the residue. The residue is dried in concentrated formic acid before being dissolved in anhydride formic acid or another strong concentrated acid, filtrated, then water is added to the filtrate to precipitate the purified chitin. The extracts from the two boilings are mixed and can either:

a: have an acid added until all astaxanthin and related carotenoids, astaxanthin esters, proteins are precipitated, whereupon the precipitate is separated from the solution by filtration or a similar process; or b: be removed to cool, after this the mixture is separated into three phases which are divided by floating off the phase with the lowest specific weight and decanting (or the equivalent) the phase with the intermediate specific weight from the phase with the highest specific weight; where the phase with the lowest specific weight is neutralized by the addition of an acid which causes the formation of two liquid phases, which are separated, and the oily phase which consists of astaxanthin esters is taken care of; where the phase with the highest specific weight is neutralized by an acid, and the solids consisting of astaxanthin and related carotenoids are filtered away and taken care of; and where the phase with the intermediate specific weight is neutralized and has marine oil, $Ca^{2+}$-ions, $S^{2-}$-ions and $(NH_4)_2HPO_4$ for the precipitation of the fluorine and the heavy metal contaminants, where this precipitate is removed from the solution by floating or the equivalent, after this the solution is acidified prior to the precipitation of the purified proteins followed by the separation of these proteins from the solution by filtration or an equivalent method.

Alternative B

The krill shell is boiled in 0.01N NaOH for 30 min. then the extract is separated from the residue. The residue is then again boiled in 0.01N NaOH for 30 min. and the extract is once more separated from the residue. The residue is then again boiled this time in 1.0N NaOH for 30 min. and the extract is again separated from the residue. The residue is dried in concentrated formic acid before being dissolved in anhydride formic acid or another strong concentrated acid, filtrated, then water is added to the filtrate to precipitate the purified chitin.

The extracts from the first two boilings in 0.01N NaOH are mixed, neutralized and have the addition of marine oil, $Ca^{2+}$-ions, $S^{2-}$-ions and $(NH_4)_2HPO_4$ for the precipitation of the fluorine and the heavy metal contaminants, where this precipitate is removed from the solution by floating or the equivalent, after this the solution is acidified prior to the precipitation of the purified proteins followed by the separation of these proteins from the solution by filtration or an equivalent method.

The extracts from the last two boilings in 1.0N NaOH are mixed and can either:

a: have an acid added until all astaxanthin and related carotenoids, astaxanthin esters, proteins are precipitated, whereupon the precipitate is separated from the solution by filtration or a similar process; or b: be placed to cool, after this the mixture is separated into three phases which are divided by floating off the phase with the lowest specific weight and decanting (or the equivalent) the phase with the intermediate specific weight from the phase with the highest specific weight; where the phase with the lowest specific weight is neutralized by the addition of an acid which causes the formation of two liquid phases, which are separated, and the oily phase consisting of astaxanthin esters is taken care of; where the phase with the highest specific weight is neutralized by an acid and solids consisting of astaxanthin and related carotenoids are filtered away and taken care of; and where the phase with the intermediate specific weight is neutralized and followed by the addition of marine oil, $Ca^{2+}$-ions, $S^{2-}$-ions and $(NH_4)_2HPO_4$ for the precipitation of the fluorine and the heavy metal contaminants, where this precipitate is removed from the solution by floating or the equivalent, after this the solution is acidified prior to the precipitation of the purified proteins followed by the separation of these proteins from the solution by filtration or an equivalent method.

EXAMPLE 2

Plants, algae and bacteria

Astaxanthin can be produced from plants, algae and bacteria that contain this die in accordance with the procedure presented in this patent.

Plants, algae or bacteria or a mixture of these can be boiled for 30 min. in 1.0N NaOH, after this the extract is separated from the residue of the plants, algae or bacteria and the extract is removed for cooling. During cooling the astaxanthin is separated and is deposited as sediment in the extract. The sediment is composed of astaxanthin and extract and these are separated by a known method.

EXAMPLE 3

Shrimps, crayfish and other crustacea

Shrimps, crayfish and crustacea differ from krill in that they are boiled before the meat is removed for consumption. The residue from the shrimps, crayfish and crustacea consists of shell, heads with contents and nonedible components, which can be processed in the same way as krill shell for the production of astaxanthin and related carotenoids, astaxanthin esters, proteins and chitin.

The above description only indicates the preferred means of applying the present invention. For specialists in the field it is obvious that various modifications can be made without exceeding the framework of the invention, which is delimited by the following claims of patent. The procedures which are indicated should therefore be considered as illustrative rather than restrictive.

It is claimed:

1. A method for recovering astaxanthin and astaxanthin carotenoids, astaxanthin esters, chitin and proteins from a raw material containing such selected from the group consisting of crustacean tissues, said method comprising the steps of extracting the crustacean raw material with boiling lye to form an alkaline extract and an extracted residue, cooling the alkaline extract to induce separation of the extract into three phases including, respectively, a lowest specific weight phase containing astaxanthin esters, an intermediate specific weight phase containing extracted proteins, and a highest specific weight phase containing astaxanthin and carotenoids, and separating at least one of the phases and processing it to concentrate the contained raw material extract.

2. The method of claim 1 wherein the raw material comprises chitin and the raw material is extracted twice with boiling lye to provide a residue comprising chitin.

3. The method of claim 2 wherein the residue is dried in concentrated formic acid and thereafter dissolved in anhydride formic acid or another strong acid, filtered and diluted with water to precipitate purified chitin.

4. The method of claim 1 wherein the phase with the highest specific weight is neutralized with an acid to precipitate astaxanthin and related carotenoids.

5. The method of claim 1 wherein the phase having the lowest specific weight is neutralized by the addition of an acid resulting in formation of two liquid phases and separating the oily phase comprising astaxanthin esters.

6. The method of claim 1 wherein the phase with the intermediate specific weight is separated and neutralized, treated to remove fluoride and heavy metallic contaminants and thereafter acidified to precipitate contained proteins.

7. The method of claim 6 wherein the neutralized phase of intermediate specific weight is purified by treatment with marine oil, $Ca^{2+}$ ions, $S^{2-}$ ions and $(NH_4)_2HPO_4$ to form a precipitate containing contaminant fluoride ions and heavy metal ions and separating the precipitate from solution prior to precipitating the protein component by acidification.

8. The method of claim 1 wherein the raw material is extracted twice with a 1.0N. solution of a strong base.

9. The method of claim 1 wherein preliminary to the initial extraction of the raw material with boiling lye the raw material is extracted at least once with a 0.1N. solution of a strong base.

10. A method for recovering chitin from a raw material containing chitin selected from the group consisting of crustacean tissues, plants, algae and bacteria, said method comprising the steps of extracting the raw material with boiling lye to form an alkaline extract and an extracted residue, drying the reside in concentrated formic acid and thereafter dissolving the residue in anhydride formic acid or another strong acid to form a solution of the residue, filtering the solution and diluting the solution with water to precipitate chitin.

11. The method of claim 10 wherein the raw material further comprises astaxanthin, astaxanthin carotenoids, astaxanthin esters and proteins, the method further comprising the step of adding an acid to the alkaline extract to precipitate astaxanthin and astaxanthin carotenoids, astaxanthin esters, and proteins.

12. The method of claim 10 wherein the lye solution used to extract the raw material is a 1.0N. solution of a strong base.

13. The method of claim 12 wherein the base is sodium hydroxide.

14. The method of claim 13 wherein the raw material further comprises astaxanthin, astaxanthin carotenoids, astaxanthin esters, and protein wherein said method the alkaline extracts are combined and cooled to produce three phases, including a phase of lowest specific weight comprising astaxanthin esters, a phase of intermediate specific weight comprising extracted proteins, and a phase of highest specific weight comprising astaxanthin and astaxanthin carotenoids.

15. The method of claim 10 wherein the raw material further comprises astaxanthin, astaxanthin carotenoids, astaxanthin esters, and proteins, said method further comprising the steps of twice extracting the raw material with a 0.01N. solution of a strong base prior to extraction of the raw material with the boiling lye solution, combining the two 0.01N. extracts, neutralizing those extracts, treating those extracts to reduce the concentration of fluoride and heavy metal ions in those extracts and acidifying the solution to precipitate extracted proteins.

* * * * *